United States Patent [19]
Reid et al.

[11] Patent Number: 5,476,771
[45] Date of Patent: Dec. 19, 1995

[54] TEST FOR QUANTITATIVE THROMBIN TIME

[75] Inventors: Thomas J. Reid, Rockville; Barbara Alving, Bethesda, both of Md.

[73] Assignee: The United States of America as represented by the Secretary of the Army, Washington, D.C.

[21] Appl. No.: 21,033

[22] Filed: Feb. 22, 1993

[51] Int. Cl.$^6$ .............................. C12Q 1/56; C12Q 1/00; G01N 33/86

[52] U.S. Cl. .................. 435/13; 435/4; 435/23; 436/69

[58] Field of Search .................. 435/13, 25, 26, 435/7, 23, 4, 7.92; 436/501, 69; 514/12, 18, 2; 424/423

[56] References Cited

U.S. PATENT DOCUMENTS

| | | | |
|---|---|---|---|
| 3,912,805 | 10/1975 | Cayzer et al. | 424/12 |
| 4,067,777 | 1/1978 | Innerfield et al. | 436/69 |
| 4,302,538 | 11/1981 | Autenrieth et al. | 435/13 |
| 4,379,142 | 4/1983 | Port et al. | 514/8 |
| 4,442,655 | 4/1984 | Stroetmann | 435/13 |
| 4,496,653 | 1/1985 | Lill et al. | 435/13 |
| 4,668,621 | 5/1987 | Doellgast | 435/13 |
| 4,767,742 | 8/1988 | Dodt et al. | 514/12 |
| 4,952,562 | 8/1990 | Klein et al. | 514/18 |
| 5,019,393 | 5/1991 | Ito et al. | 424/423 |
| 5,053,453 | 10/1991 | Ku | 530/814 |
| 5,118,790 | 6/1992 | Winant et al. | 514/12 |
| 5,187,102 | 2/1993 | Stocker et al. | 436/69 |
| 5,196,404 | 3/1993 | Maraganone et al. | 514/13 |

FOREIGN PATENT DOCUMENTS

| | | | |
|---|---|---|---|
| 1508169 | 9/1989 | U.S.S.R. | 436/69 |
| 8606840 | 11/1986 | WIPO | 436/69 |

OTHER PUBLICATIONS

Haver, et al., "Characterization of Thrombin–Induced Contraction . . . ", *Blood Vessels* 21:53–63 (1984).
Lefkovitz, et al., "Direct Thrombin Inhibitors . . . ", *Circulation* 90; No. 3, 1522–1536 (1994).
Markwardt, "Hiradin and Derivatives as Anticoagulant Agents", *Thombosis and Haemostasis*, Stuttgart, 1993.
Trapodi, et al., "Effects of Hirudin on Activated Thromboplastin . . . ", *Thrombosis and Haemostasis*, Stuttgartt, 1993.
Zoldhelyi, et al., "Recombinant Hiradinin Patients . . . ", *Circulation* 88:#5, 2015–2022 (1993).
Murphy et al.; Am–J–Physiol. 1980 Dec.; 239(6):H742–50. (Abstract).
Fenton et al., Clin. Chem. 32/2, 320–324 (1986).

*Primary Examiner*—David A. Redding
*Assistant Examiner*—Louise N. Leary
*Attorney, Agent, or Firm*—John F. Moran

[57] ABSTRACT

A quantitative method for determining the plasma levels of thrombin-specific inhibitors is based on the quantitative thrombin time using plasma dilutions, excess fibrinogen and thrombin. The plasma dilutions and excess fibrinogen act in concert to eliminate the effects that coagulopathies have on standard coagulation tests. The method is relatively simple and provides superior results to standard conventional tests. The method is suitable for performance in clinical hematology laboratories on a routine basis using commercially available instrumentation.

6 Claims, 4 Drawing Sheets

TEST FOR QUANTITATIVE THROMBIN TIME

FIELD OF THE INVENTION

This invention relates to laboratory testing useful in monitoring of anticoagulant therapy. More specifically, this invention relates to assays for the anticoagulants that are known to inhibit the enzyme thrombin.

BACKGROUND OF THE INVENTION

Presently, thrombin-specific inhibitors are in clinical trials as anticoagulant drugs for the treatment of arterial (after coronary artery angioplasty) and deep venous thrombosis. The specificity of these drugs is reflected in the dissociation constants ranging from 2 picomoles/L - 2 nanomoles/L. The thrombin specific inhibitors have demonstrated efficacy in animal models for both treatment and prevention of arterial and venous thrombosis. Recombinant hirudin, derived from the medicinal leech *Hirudo medicinalis*, is the thrombin-specific inhibitor most studied. Effective doses and their range for therapeutic plasma levels in humans have been determined. The low and high ends of the range are used for venous and arterial thrombosis, respectively.

Several U.S. patents have been issued on anti-thrombin agents for use as medicinals or bound to implantable materials. U.S. Pat. No. 4,944,943 to Eschenfelder, et al. teaches use of hirudin and t-PA for treatment of thrombosis. U.S. Pat. No. 4,952,562 to Klein, et al, discloses anti-thrombotic peptides and pseudopeptides. U.S. Pat. No. 5,019,393 to Ito, et al. teaches use of implantable materials having a thrombogenesis inhibitor immobilized thereon. U.S. Pat. No. 5,053,453 to Ku discloses hirudin or hirudin derivatives covalently linked to support materials to avoid formation of thrombi. U.S. Pat. No. 5,640,814 to Klein, et al. discloses an anti-thrombotic peptide for administration as a medicinal. U.S. Pat. No. 5,087,613 to Courtney, et al. discloses hirudin variants for use as inhibitors of thrombin activity. U.S. Pat. No. 5,095,092 discloses a process for isolation and purification of hirudin. None of the cited patents disclose a quantitative thrombin-time test as taught herein.

Several methods are presently used to assess whether the patient taking the new thrombin-specific inhibitors is therapeutically anticoagulated. It is possible to measure plasma thrombin-specific inhibitors levels by high performance liquid chromatography (HPLC). Though accurate, HPLC is generally available only in large referral hospitals and commercial labs and requires a high level of staff expertise. Even when available in large referral hospitals, the technique is time consuming. Hence, there is delay in obtaining results. This delay is unacceptable when a clinical practitioner is attempting to closely monitor and control the progress of the patient.

Another approach is to monitor the prolongation of the activated partial thromboplastin time (APTT). The APTT is a standard screening test of the coagulation system. This test is commonly used to follow the degree of anticoagulation in patients receiving the anticoagulant heparin. However, in the absence of specific thrombin inhibitors a variety of coagulopathies [e.g. isolated or multiple factor deficiency, abnormal fibrinogen, decreased fibrinogen concentration or antiphospholipid antibodies] tend to prolong the APTT results. Some patients with coagulopathies associated with the nephrotic syndrome or the lupus anticoagulant also develop thrombosis requiring treatment with anticoagulants. In these cases, the APTT is already prolonged and cannot be used to monitor anticoagulation with thrombin specific inhibitors.

Another clotting assay, the standard thrombin time, is routinely used in a qualitative fashion in clinical laboratories to determine the presence of heparin and abnormal or low levels of fibrinogen. The standard thrombin time is not effective and has not been used to quantitate the concentrations of thrombin-specific inhibitors in the blood because of the inherent sensitivity of the standard thrombin time, as presently developed, to factors other than these inhibitors (Walenga J. M. et al. Seminars in Thrombosis Hemostasis 17:103, 1991). In addition, plasmas obtained from patients with liver disease, dysfibrinogenemia, hypofibrinogenemia, or who have received fibrinolytic therapy are likely to produce a prolonged standard thrombin time.

Besides HPLC and the APTT, further methods including amidolytic assays for thrombin and immunologic assays for the hirudinthrombin complex have been suggested. However, the techniques are not easily applied to the clinical laboratory. Because of the potential therapeutic efficacy of the thrombin-specific inhibitors, a new and improved laboratory test for determining plasma levels that can be performed in clinical laboratories with presently available instrumentation is needed. Furthermore, such a new process capable of providing results that are easily interpreted by clinical practitioners would be of great utility.

SUMMARY OF THE INVENTION

A novel clinically useful test for monitoring patients on thrombin-specific inhibitor (TSI) therapy, a quantitative thrombin time (QTT) for the management of anticoagulation with thrombin-specific inhibitors, based on the specificity of the TSI for thrombin is disclosed and claimed herein.

The object of the present invention is to provide a method to measure thrombin time that will not be affected by presence of abnormal plasmas which cause a prolongation of standard tests (APTT and standard thrombin time, vide supra), but will be sensitive to the presence of thrombin-specific inhibitors. Another object of the invention is to provide a method from which unknown plasma concentrations of thrombin-specific inhibitors can be determined by generating a standard curve for the therapeutic range of the inhibitor using the QTT. A related object is to provide a method which can be readily performed on laboratory instruments commonly used for measuring the standard thrombin time.

DETAILED DESCRIPTION OF THE INVENTION

Figure 1:
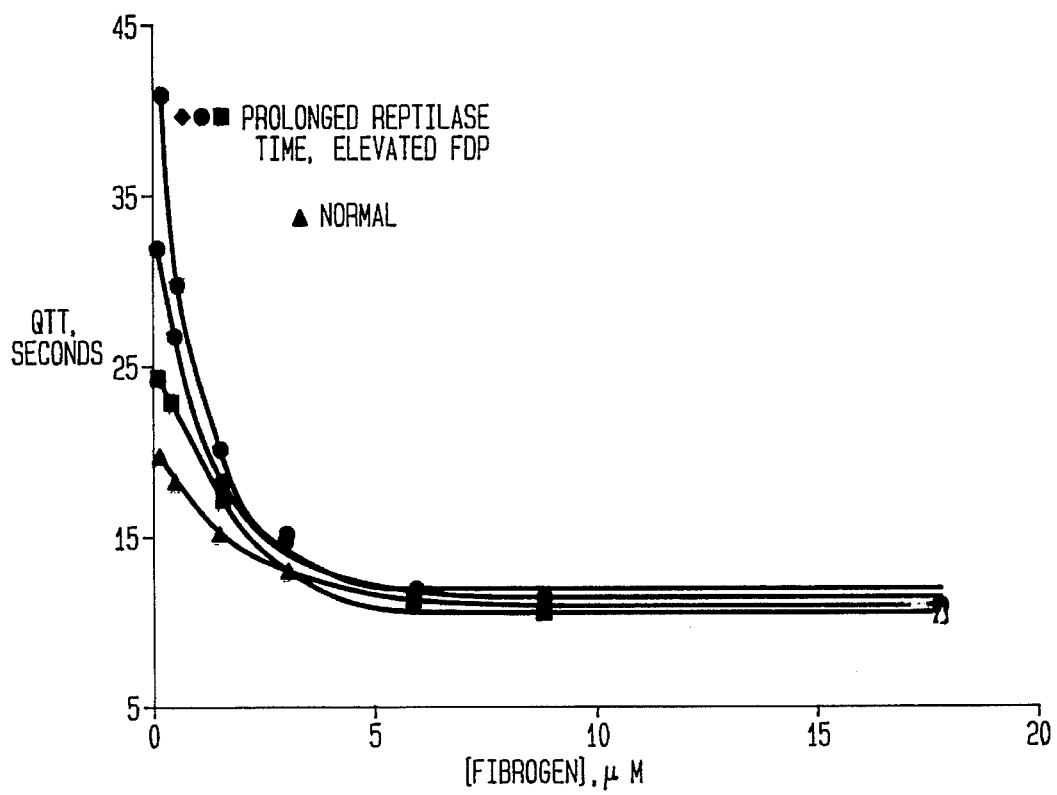
FIG. 1 shows the effect of concentration of the purified fibrinogen on the quantitive thrombin time in abnormal plasmas with prolonged reptilase times and elevated FDP and in normal plasma.

This invention provides a novel method for the quantitative determination of plasma levels of thrombin-specific inhibitors by specifically measuring thrombin time in the presence of exogenous fibrinogen and thrombin. Normal plasmas and plasmas with a coagulopathy have the same baseline for thrombin-specific coagulation time when tested by the QTT. By eliminating the interfering effects of factors in the plasmas from patients with coagulopathy, the prolongation of the QTT will depend only on the presence of thrombin-specific anticoagulant present in the sample and will, therefore, provide a method for evaluation of the anticoagulant independent of other plasma abnormalities that could affect the thrombin time. To eliminate the effect of abnormalities such as antiphospholipid antibodies, and factor deficiencies, the phospholipid based APTT was abandoned in favor of the thrombin-based assay which is independent of phospholipid and coagulation factors other than fibrinogen. Only fibrin degradation products, heparin, and abnormal fibrinogens or a decreased fibrinogen potentially present in plasma could interfere with the assay. The effect of these abnormalities can be removed by diluting plasma 1:10 in buffer and adding excess fibrinogen.

While the test developed has been shown to be effective when using other thrombin-specific inhibitors, the inhibitor exemplified in the testing disclosed herein was recombinant hirudin. Quantification was tested by adding recombinant hirudin to normal plasma at different concentrations within the known therapeutic range. The QTT was then tested with these plasmas and a linear relationship was shown between the log (QTT) and concentration of recombinant hirudin. This allowed the determination of concentrations of recombinant hirudin in plasma. The specificity of the QTT was assessed by adding a known concentration of recombinant hirudin to patient plasma samples demonstrating a coagulopathy (prolonged APTT and/or standard thrombin time). The expected and observed values of recombinant hirudin levels were then compared and shown to be compatible with use of the QTT in the clinical monitoring of patients on recombinant hirudin. It was shown, by comparative evaluation, that the APTT does not provide the specificity provided by the inventive method.

The technique was performed using two different commercially available instruments and equivalent results were obtained.

Methods and Materials

Materials

Plasmas were those submitted to the coagulation laboratory for evaluation of abnormal screening coagulation studies and from healthy volunteers who gave informed consent under a protocol approved by the Human Use Committee of the Walter Reed Army Institute of Research. Human alpha-thrombin (specific activity 2,000–4,000 NIH units/mg protein), recombinant hirudin (specific activity 8,500 units/mg protein) and reptilase (ATROXIN) were purchased from Sigma Chemical Company (St Louis, Mo.). Human fibrinogen was supplied by KabiVitrum (Stockholm, Sweden). APTT reagent was purchased from Organon Teknika Corporation (Durham, N.C.). Sodium heparin (1000 U/mL) was purchased from Elkins-Sinn, Incorporated (Cherry Hill, N.J.).

Blood sample preparation:

Blood samples were collected into plastic tubes containing balanced citrate as the coagulant in a ratio of one part anticoagulant to nine parts blood. Each sample was centrifuged at 4° C. and 10,000×g for 20 minutes to obtain platelet-poor plasma which was then stored at −70° C. until ready for use.

Standard thrombin time

The thrombin time was measuring the time to clot formation after adding 100 µL of a 5 U/mL solution of alpha thrombin to 100 µL of plasma and 100 µL VS buffer (vide infra). Either a dataclot-2 fibrometer (Helena Laboratories, Beaumont, Tex.) or an ST4 coagulation instrument (Diagnostica Stago, Parsippany, N.J.) was used.

Quantitative thrombin time (QTT)

Human alpha-thrombin was diluted to a concentration of 2.5–20 U/mL in veronal-saline-calcium (VSC) buffer (2.8 mM sodium diethylbarbiturate, 100 mM sodium chloride, 25 mM calcium chloride, pH 7.35) that also contained 1% human serum albumin. Fibrinogen concentrations (0.1–18 µM) were made in VS buffer (as VSC buffer except the buffer contained no calcium, and sodium chloride concentration was 144 mM). Plasma samples were diluted 1:10 in VS buffer. The plasma dilutions, alpha-thrombin and fibrinogen solutions were incubated separately at 37° C. for six minutes before using. Equal volumes of plasma samples and fibrinogen were mixed and incubated at 37° C. for one minute. 200 µL of the plasma-fibrinogen mixture were removed and placed in an assay well. The thrombin time was measured as the time to clot formation after adding 100 µL of the alpha-thrombin solution. Instruments used for the standard thrombin time were also used for the QTT.

APTT assay

The APTT assay was done using a CP-8 photooptic coagulation profiler (BIODATA Corporation, Willow Grove, Pa). 100 µL of plasma was incubated with 100 µL APTT reagent for six minutes. The APTT was measured as the time of clot formation after adding 100 µL 25 mM $CaCl_2$.

Reptilase time

The reptilase time was done using a dataclot-2 fibrometer. 100 µL of reconstituted reptilase was added to 200 µL of plasma and the clotting time was recorded.

Preparation of plasma samples for standard curve determination

Recombinant hirudin (lyophilized preparation) was diluted in normal pooled plasma to a concentration of 50 µg/mL. Further dilutions in normal plasma were made to obtain concentrations within the therapeutic range (0.1–3 µg/mL).

Standard curve

The log of the QTTs were calculated and a standard curve was generated after linear regression by plotting the log (QTT) vs concentration of recombinant hirudin (µg/mL). From the standard curve, an unknown plasma level of recombinant hirudin can be determined.

Preparation of plasma samples for determining effect of heparin concentration on the QTT Heparin (initial concentration 1000 u/mL) was diluted in normal pooled plasma to a concentration of 10 U/mL. Further dilutions in plasma were made to obtain heparin concentrations of 0.1–8 U/mL.

The QTT in normal plasma samples

The results of the QTT from twenty normal individuals (ten male, ten female) are shown in Table 1; all had a normal standard thrombin time and APTT.

TABLE 1

Summary statistics based on plasmas from twenty normal individuals, ten male and ten female. All plasma samples had normal APTT and standard thrombin time, using standard procedures (see text).

| | |
|---|---|
| Mean Quantitative Thrombin Time, seconds | 13.9 |
| s.e.m.[a], seconds | 0.14 |
| s.d.[b], seconds | 0.66 |
| range (mean +/− 2xs.d.), seconds | 12.6–15.2 |
| r.m.s.[c] difference, % | 4.6 |

[a]standard error of the mean; [b]standard deviation; [c]root mean square difference

Effect of fibrinogen concentration on the QTT

The effect of concentration of purified fibrinogen on the quantitative thrombin time in plasma and abnormal plasmas was determined. Different fibrinogen concentrations were used in the quantitative thrombin time to determine at which concentration the effects of the abnormal plasmas were eliminated.

Procedure

Figure 2:
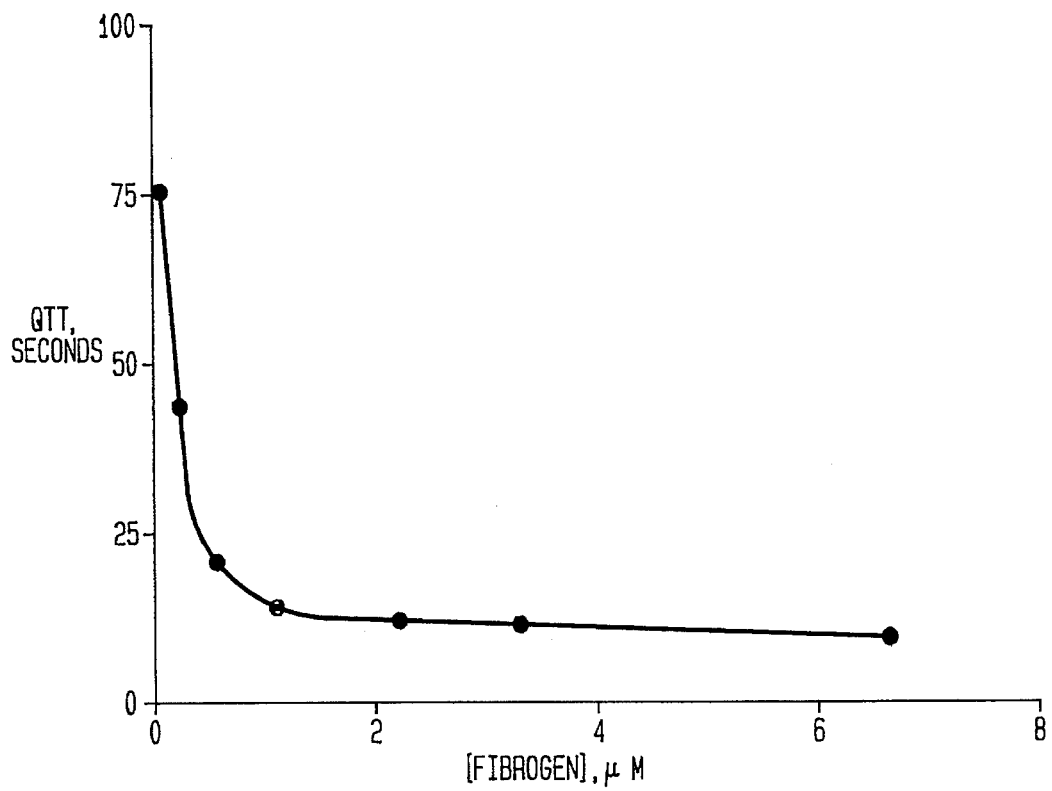
FIG. 2 shows the effect of concentration of purified fibrinogen on the quantitative thrombin time in plasma with low fibrinogen levels.

Plasmas were diluted 1:10 in buffer; 100 μL of the diluted plasma was added to 100 μL purified human fibrinogen at different concentrations (0.1–18 μM) and incubated for 30 seconds; 100 μL of 5 U/mL human alpha-thrombin was added to start the reaction; the clotting time was measured. The addition of excess fibrinogen in the assay eliminated the effects of abnormal fibrinogens (FIG. 2) and low fibrinogen (FIG. 2, insert). Plasmas with an abnormal fibrinogen (dysfibrinogenemia: standard thrombin time=45.2 and 18.5 sec [normal 11–14], reptilase time=22.6 and 15.5 sec [normal 8–11]), low fibrinogen (hypofibrinogenemia: fibrinogen=38 mg/dL [normal 200–400]) and plasma with increased fibrin degradation products (FDP=1024 μg/mL [normal<10 μg/mL]) and low fibrinogen (fibrinogen=112 mg/dL) were evaluated. The optimal fibrinogen concentration was determined to be 9–18 μM. This concentration was more than sufficient to overcome the effects of abnormal plasma samples.

Effect of diluting plasma tin buffer) on the QTT

Diluting the plasma samples 1:10 in buffer mitigated the effects of fibrin degradation products and therapeutic heparin levels (Table 2). The presence of antiphospholipid antibodies did not interfere with the assay.

Procedure

Plasmas were diluted 1:10 in buffer; 100 μL of the diluted plasma was added to 100 μL 9 μM purified human fibrinogen and incubated for 30 seconds; 100 μL of 5 U/mL human alpha-thrombin was added to start the reaction; the clotting time was measured. Table 2. Coagulopathies that might otherwise interfere with standard clotting tests, do not interfere with the quantitative thrombin time.[a]

TABLE 2

| Coagulopathy | Quantitative Thrombin Time[b], sec | Standard Thrombin Time[c], sec | APTT[d], sec |
|---|---|---|---|
| Abnormal fibrinogen (dysfibrinogenemia)[e] | 14.2 | 59.1* | 29.4 |
| Abnormal fibrinogen (dysfibrinogenemia)[f] | 14.8 | 45.2* | 35.7* |
| Abnormal fibrinogen (dysfibrinogenemia)[g] | 14.4 | 18.5* | 43.3* |
| Abnormal fibrinogen (dysfibrinogenemia)[h] | 13.6 | 16.0* | 37.5* |
| Increased fibrin degradation products[i] | 14.2 | 23.5* | 43.0* |
| Increased fibrin degradation products[j] | 14.2 | 22.4* | 74.8* |
| Multiple Factor Deficiencies[k] | 13.8 | 13.8 | 57.6* |
| Heparin therapy[l] | 14.4 | >120* | 64.2* |
| Low fibrinogen[m] | 14.2 | 25.8* | >120* |
| Antiphospholipid Antibody | 14.2 | 12.3 | 50.1* |
| Antiphospholipid Antibody | 14.4 | 13.5 | 44.4* |
| Antiphospholipid Antibody | 13.2 | 12.2 | 57.9* |
| Antiphospholipid Antibody | 13.2 | 13.7 | 65.3* |
| Antiphospholipid Antibody | 13.6 | 12.8 | 90.0* |
| Low factor XII[n] | 14.2 | 14.0 | 45.2* |

*Abnormal value. [b]Normal: 12.6–15.2 seconds; [c]normal: 11–14 seconds; [d]normal: 22–34 seconds. [e]reptilase time = 29.4 sec (normal 8–11); [f]reptilase time = 22.6; [g]reptilase time = 15.5; [h]reptilase time = 15.2; [i]fibrin degradation products = 128 μg/mL (normal < 10), fibrinogen = 225 mg/dL (normal 200–400); [j]fibrin degradation products = 1024 μg/ml, fibrinogen = 112 mg/dL; [k]factor II = 37%, factor X = 16% (normal 50–150); [l]0.5 U heparin/mL; [m]fibrinogen = 38 mg/dL; [n]factor XII < 10% (normal 50–150).

Effect of heparin concentration on the QTT

Figure 3:
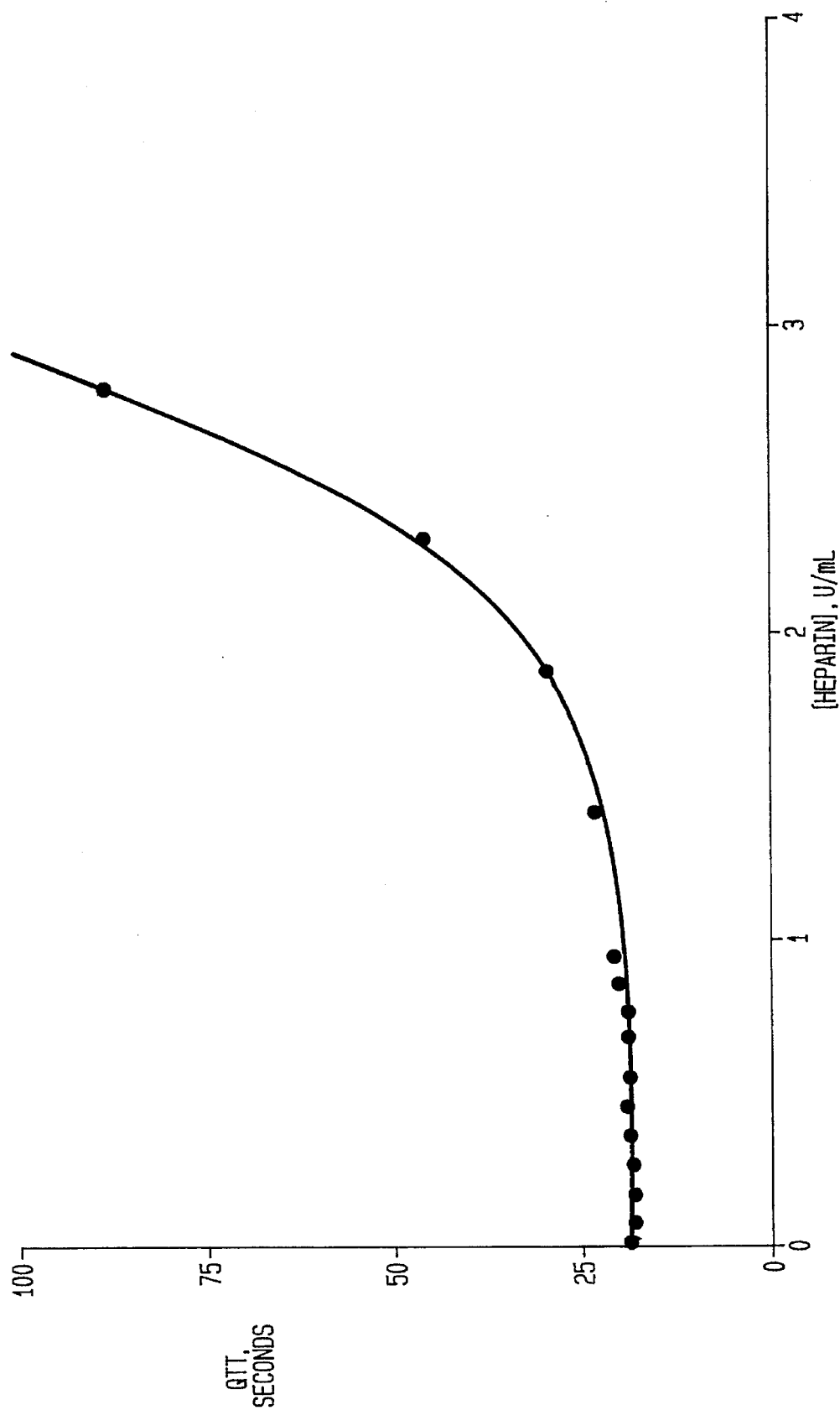
FIG. 3 shows the effect of heparin concentration on the QTT.

Normal plasma supplemented with heparin at various concentrations were tested in the QTT. Procedure: Plasma was supplemented with porcine heparin at different concentrations (0.1–10 U/mL); these plasmas were diluted 1:10 in buffer; 100 μL of the diluted plasma was added to 100 μL purified human fibrinogen 9 μM) and incubated for 30 seconds; 100 μL of 5 U/mL human alpha-thrombin was added to start the reaction; the clotting time was measured. The QTT became sensitive to heparin at 0.8 U/mL (FIG. 3). The therapeutic range for heparin is 0.3–0.5 U/mL.

Standard curve for recombinant hirudin using the QTT

The quantitative thrombin time was determined for different known concentrations of recombinant hirudin in plasma. A standard curve was developed by plotting the LOG (quantitative thrombin time) vs concentration of recombinant hirudin. Procedure: Plasma was supplemented with purified recombinant hirudin at different concentrations (0.1–1.75 μg/mL); these plasmas were diluted 1:10 in buffer; 100 μL of the diluted plasma was added to 100 μL purified human fibrinogen (9 μM) and incubated for 30 seconds; 100 μL of human alpha-thrombin (5 U/mL) was added to start the reaction; the clotting time was measured.

Figure 4:
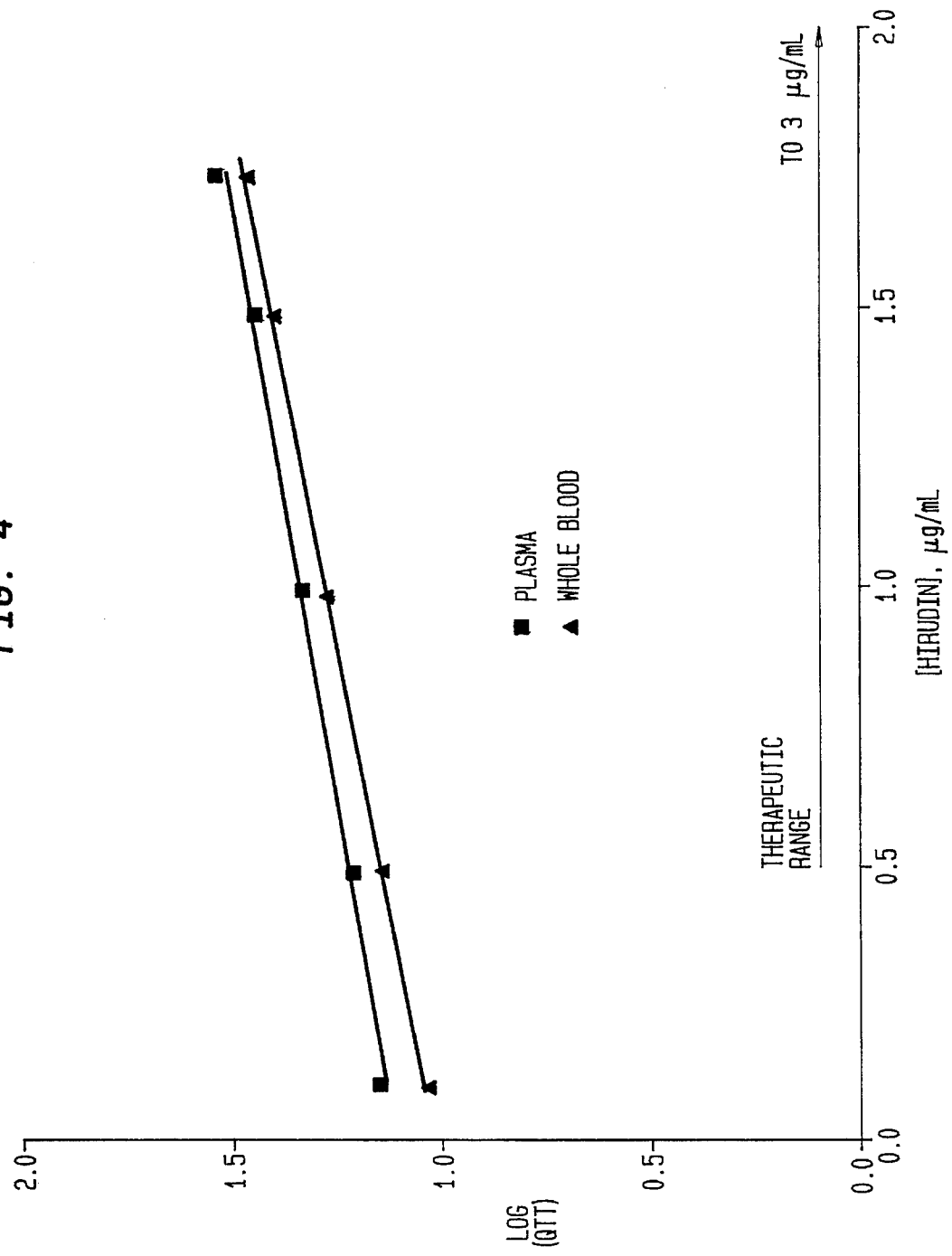
FIG. 4 is the standard curve for recombinant hirudin using the quantitative thrombin time.

Several thrombin concentrations were tested in developing assays for recombinant hirudin. Low thrombin concentrations were too sensitive to high therapeutic plasma levels of recombinant hirudin whereas high thrombin concentrations were insensitive to low therapeutic levels. There was no thrombin concentration that was effective over the entire therapeutic range of recombinant hirudin. Therefore, a thrombin concentration (5 U/mL) sensitive at the low therapeutic range (0.1–1.75 μg/mL) of recombinant hirudin was selected (FIG. 4). The hirudin-free plasma data point was not included in the standard curve. To assay hirudin concentrations greater than 1.75 μg/mL, a 1:1 dilution in pooled plasma was required before the 1:10 dilution in the assay. The optimal conditions for the QTT were: 100 μL 1:10 plasma dilution, 100 μL fibrinogen (9 μM) and 100 μL alpha-thrombin (5 U/mL).

Validity of the QTT in determining plasma concentrations of recombinant hirudin The validity of the QTT in determining plasma recombinant hirudin levels was assessed by adding known concentrations of recombinant hirudin to abnormal and normal pooled plasma. The QTT was measured and the recombinant hirudin concentration determined from the standard curve described above. Table 3 demonstrates that a number of coagulopathies that may prolong the standard thrombin time do not interfere with the measurement of recombinant hirudin levels as determined by the QTT.

Procedure

Plasma was supplemented with purified recombinant hirudin at different concentrations (0.1–1.75 μg/mL); these plasmas were diluted 1:10 in buffer; 100 μL of the diluted plasma was added to 100 μL purified human fibrinogen (9 μM) and incubated for 30 seconds; 100 μL of 5 U/mL human alpha-thrombin was added to start the reaction; the clotting time was measured.

TABLE 3

| Coagulopathy | QTT, seconds | Measured concentration of recombinant hirudin, μg/mL | % Error[a] |
|---|---|---|---|
| Antithrombin III[b] deficiency | 22.6 | 1.11 | 11 |
| Low Factor XII[c] | 23.8 | 1.21 | 3.1 |
| Abnormal fibrinogen dysfibrinogenemia[d] | 21.7 | 1.04 | 17.0 |
| Abnormal fibrinogen dysfibrinogenemia[e] | 27.8 | 1.49 | 19.5 |
| Abnormal fibrinogen dysfibrinogenemia[f] | 23.8 | 1.21 | 3.2 |
| Elevated fibrin degradation products[g] | 24.0 | 1.22 | 2.2 |
| Elevated fibrin degradation products[h] | 22.4 | 1.1 | 12.3 |
| Elevated fibrin degradation products[i] | 25.5 | 1.34 | 7.0 |
| Low fibrinogen[j] | 24.4 | 1.25 | 0 |
| Heparin therapy[k] | 26.1 | 1.38 | 10.4 |
| Multiple factor deficiencies[l] | 24.6 | 1.27 | 1.6 |
| Antiphospholipid Antibody | 24.4 | 1.25 | 0 |
| Antiphospholipid Antibody | 22.4 | 1.11 | 12.3 |
| Antiphospholipid Antibody | 22.5 | 1.1 | 11.7 |

Recombinant hirudin was added to all plasma samples at a final concentration of 1.25 μg/mL.

$a \dfrac{\text{expected} - \text{measured}}{\text{expected}} \times 100 = \dfrac{1.25\ \mu g/mL - \text{measured}}{1.25\ \mu g/mL} \times 100$

[b]Antithrombin III = 54% (normal 88–140);
[c]factor XII < 10% (normal 50–150);
[d]standard thrombin time = 18.5 sec (normal 11–14), reptilase time = 15.5 sec (normal 8–11);
[e]standard thrombin time = 45.2 sec, reptilase time = 22.6 sec;
[f]standard thrombin time = 18.1 sec, reptilase time = 13.1 sec;
[g]fibrin degradation products = 1024 μg/mL (normal <10), fibrinogen = 183 mg/dL (normal 200–400);
[h]fibrin degradation products = 256 μg/mL, fibrinogen = 360 mg/dL;
[i]fibrin degradation products = 1024 μg/mL, fibrinogen = 112 mg/dL;
[j]fibrinogen = 38 mg/dL;
[k]0.5 U heparin/mL;
[l]factor II = 37%, factor X = 16% (normal 50–150).

Standard curve for recombinant hirudin using the APTT

The effect of recombinant hirudin concentrations on the APTT was measured. Normal plasma was supplemented with recombinant hirudin at various concentrations and the APTT was measured.

Procedure

Plasma was supplemented with purified recombinant hirudin at different concentrations (0.1–4 μg/mL); 100 μL of the APTT reagent was added to 100 μL of the plasma supplemented with recombinant hirudin and incubated for 6 minutes; 100 μL of 25 mM CaCl$_2$ was added to start the reaction; the clotting time was measured. FIG. 4 demonstrates that the APTT is not useful at the low end of the therapeutic ranges for recombinant hirudin.

Procedure

Plasma was supplemented with purified recombinant hirudin at different concentrations (0.1∝4 μg/mL); 100 μL of the APTT reagent was added to 100 μL of the plasma supplemented with recombinant hirudin and incubated for 6 minutes; 100 μL of 25 mM CaCl$_2$ was added to start the reaction; the clotting time was measured.

Table 4 conclusively shows that the presence of a lupus anticoagulant, abnormal fibrinogens, heparin and fibrin degradation products interfere with the APTT assay for the recombinant hirudin.

TABLE 4

Coagulopathies that interfere with the APTT, interfere with the determination of plasma levels of recombinant hirudin as performed with the APTT.[a]

| Coagulopathy | APTT, seconds | Measured concentration of recombinant hirudin, μg/mL | % Error[b] |
|---|---|---|---|
| Low fibrinogen[c] | >300 | — | — |
| Abnormal fibrinogen (dysfibrinogenemia)[d] | 105.8 | 1.93 | 54 |
| Abnormal fibrinogen (dysfibrinogenemia)[e] | 132.0 | 3.66 | 169 |
| Increased fibrin degradation products[f] | 182.1 | 6.97 | 458 |
| Increased fibrin degradation products[g] | 108.8 | 2.13 | 70 |
| Heparin therapy[h] | >300 | — | — |
| Low factor XII[i] | 103.4 | 1.77 | 42 |
| Antiphospholipid Antibody | 117.7 | 2.72 | 118 |
| Antiphospholipid Antibody | 115.6 | 2.58 | 106 |
| Antiphospholipid Antibody | 162.4 | 5.67 | 354 |

Recombinant hirudin was added to all plasma samples at a final concentration of 1.25 μg/mL.
[a]indicates value could not be determined.

$$b \frac{\text{expected} - \text{measured}}{\text{expected}} \times 100 = \frac{1.25\ \mu g/mL - \text{measured}}{1.25\ \mu g/mL} \times 100$$

[c]fibrinogen = 38 mg/dL (normal 200–400);
[d]standard thrombin time = 45.2 sec (normal 11–14), reptilase time = 22.6 sec (normal 8–11);
[e]standard thrombin time = 18.5 sec, reptilase time = 15.5 sec.,
[f]fibrin degradation products = 1024 μg/mL (normal <10), fibrinogen = 112 mg/dL;
[g]fibrin degradation products = 256 μg/mL, fibrinogen = 360 mg/dL;
[h]0.5 U heparin/mL;
[i]factor XII <10% (normal 50–150).

Comparison of results from the QTT and APTT using abnormal plasmas supplemented with recombinant hirudin The mean errors for determining the concentration of recombinant hirudin in abnormal plasma using the QTT were less than 10%. In contrast, using the same plasmas, the measured concentration of recombinant hirudin using the standard APTT showed no agreement with the expected value (Table 5).

TABLE 5

Summary of Data for validation of the QTT in different clinical conditions.

| | QTT | APTT |
|---|---|---|
| r.m.s.* difference recombinant hirudin concentration, μg/mL | 0.12 | 2.82 |

TABLE 5-continued

Summary of Data for validation of the QTT in different clinical conditions.

| | QTT | APTT |
|---|---|---|
| r.m.s. error, % | 9.8 | 225 |

*root mean square

Figure 5:
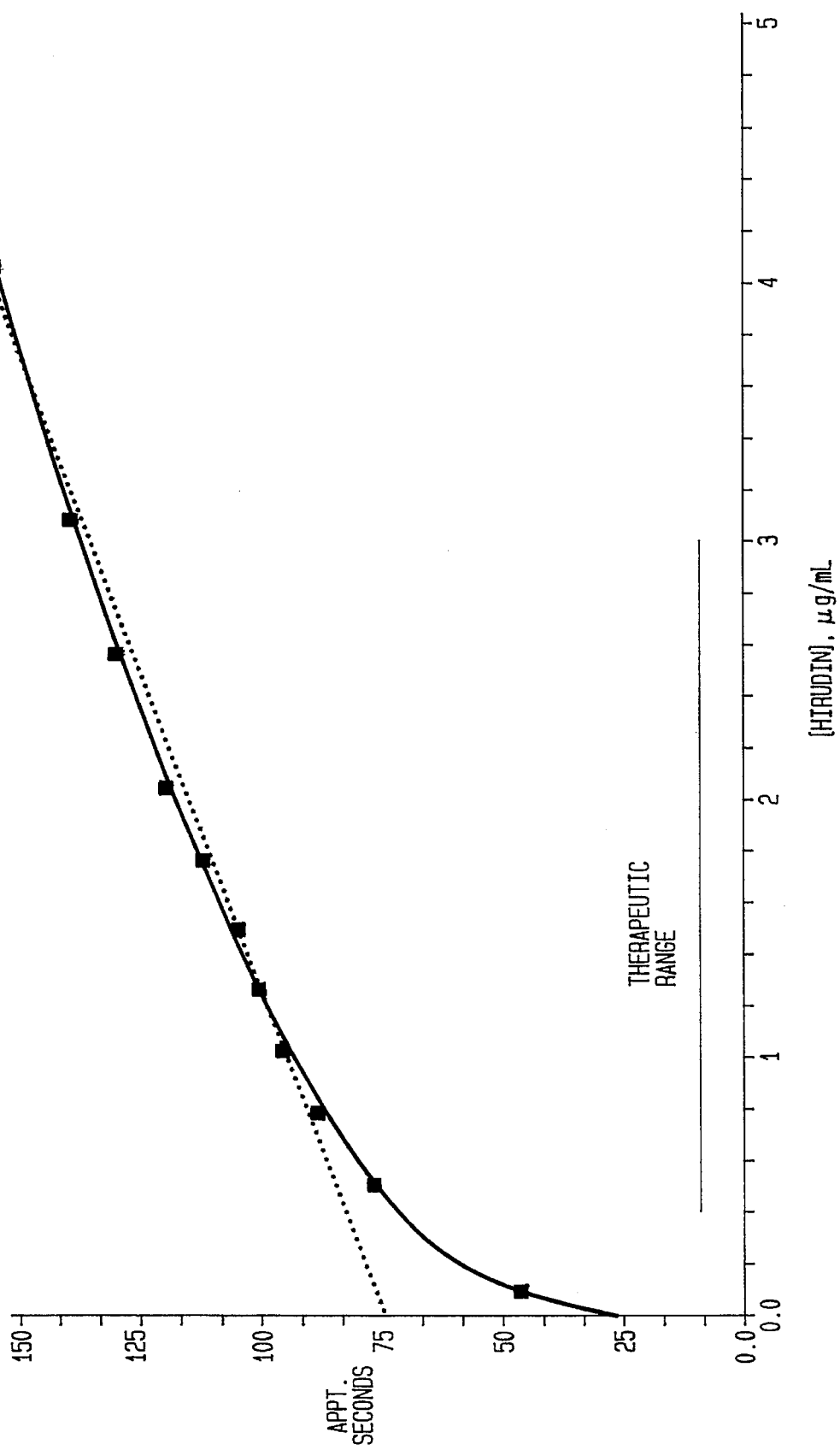
FIG. 5 shows the effect of recombinant hirudin concentration on the APTT.

The thrombin-specific inhibitor hirudin and its analogues have demonstrated efficacy in the prevention of thrombosis in preclinical studies. The anticoagulant effects have been monitored by the APTT because the standard thrombin time is too sensitive to the agents to be of clinical utility. The APTT has two major problems that limit its usefulness in monitoring recombinant hirudin: 1) patients with a prolonged baseline APTT cannot be followed (this also holds true for patients receiving heparin therapy); and 2) there is a nonlinear dose-response at low therapeutic levels of recombinant hirudin with regard to the APTT (FIG. 5). The clinical consequence of using the APTT to monitor therapy in the low therapeutic range is excessive anticoagulation for the specific clinical condition. We have developed a quantitative thrombin time that eliminates the inherent difficulties associated with the APTT and the standard thrombin time. The problems which the invention is designed to solve are the sensitivity of standard tests to therapeutic heparin levels, low levels of fibrinogen, abnormal fibrinogens and fibrin degradation products, lupus anticoagulant (antiphospholipid antibodies), and low plasma factor levels.

Some of the novel aspects of the invention include 1) the addition of fibrinogen in excess to compensate for abnormal or low fibrinogen and 2) the plasma samples are diluted 1:10 in buffer which effectively prevents interference of fibrin degradation products, abnormal fibrinogen and heparin. There are several distinct advantages of the invention. The method is simple and can be done in any lab that performs thrombin times routinely (most hospitals). The procedure is specifically adapted for use on instruments presently available to clinical laboratories. The newer automated equipment and methods used in determination of thrombin time may be used for practice of the invention. The method is also quick and requires no additional expertise above that already available in the clinical laboratory. A small amount of patient material is needed (25–50 μL of plasma for 4 tests); where standard tests require 100 μL for a single test. The method allows quantitation of plasma levels of recombinant hirudin and other thrombin-specific inhibitors for use with other thrombin-specific inhibitors (e.g. synthetic or semisynthetic analogues of recombinant hirudin). The mean error is less than 10%. The standard curve is linear in the therapeutic range, where standard tests are either not linear in the low therapeutic range (APTT) or are too sensitive to recombinant hirudin (standard thrombin time). The method is more sensitive to thrombin-specific inhibitors in comparison to standard tests, as demonstrated by the response of the clotting times to recombinant hirudin concentrations. Finally, the test is inexpensive and fast in comparison to HPLC.

While normal human thrombin was used in the procedure as exemplified, mutant or normal thrombin from other sources may be used in the QTT so long as the alternate thrombin provides a reliable dosage curve when tested against the specific thrombin-specific inhibitor for which concentration is being determined. Similarly, the fibrinogen can be from any source so long as the fibrinogen is functional in normal clot formation. Although a veronal based buffer was used in the development of the QTT, any buffer that provides a reliable dosage curve when tested against a TSI can be used.

The materials for the QTT may be sold as kits. The following components could be provided in the kit:

1) One or more vials of lyophilized plasma containing a known amount of thrombin-specific inhibitor (TSI) which may contain protamine sulfate should be provided. The contents of the vial(s) may be reconstituted with water so that the final concentration of the TSI is such that serial dilutions allow for TSI within the therapeutic range. The addition of the protamine sulfate may be used to effectively remove heparin from the reaction. If protamine sulfate is used, a preferred concentration in the final diluted TSI-containing solution would be about 120 µg/mL. However, in some instances the TSI may be available to laboratories as a stock solution(s).

2) One or more vials of lyophilized alpha-thrombin which may be formulated with a stabilizing agent such as albumin and may contain buffer should be provided. The thrombin could be reconstituted with water to provide the desired concentration.

3) One or more vials of lyophilized fibrinogen to be reconstituted to a final concentration of about 4.75 µM (160 mg/dL). The plasma may contain a neutralizing agent such as protamine sulfate. The kit can, if desired, hold a separate vial of protamine sulfate or another heparin neutralizing agent to be used with TSI and patient samples when a patient is on heparin therapy.

4) Vials of buffer for diluting samples may be included.

Using the kit items, the following procedure may be followed. In a preferred embodiment the standard curve may be developed to identify effective levels of TSI by the following method:

a. Preparing serial dilutions of a thrombin-specific inhibitor in normal plasma in known concentrations to provide samples (though a kit containing varying amounts of TSI within the appropriate range will avoid this procedure).

b. Dilute the samples in buffer to provide 1:10 dilutions.

c. Mixing the dilutions with a 9–18 µM solution of purified human fibrinogen to provide samples.

d. Adding a 5 U/mL solution of purified human alpha-thrombin to the samples of step c to provide solutions.

e. Measuring the clotting times of the solutions in step d.

f. Plotting a standard curve from the results obtained from step e.

The level of TSI concentration in patient plasma is tested in the following manner to determine the TSI level in the patient:

1. Diluting in buffer a plasma sample from patients receiving a thrombin-specific inhibitor to provide a 1:10 plasma to buffer concentration.

2. Mixing the patient samples with a solution of fibrinogen.

3. Adding a thrombin solution to the patient samples prepared in step 2.

4. Measuring the clotting times of the solutions of step 3.

5. Determining the concentration of the inhibitor in the patient samples using the standard curve previously developed.

The invention may also be practiced using whole blood rather than patient plasma.

Vials containing varying amounts of the TSI required for generating the standard curve would be made by diluting the TSI to provide varying dilutions for use in determining the curve. The normal plasma is reconstituted by dilution with buffered water (or the buffer may be added into the diluent) to provide varying concentrations of TSI. A second set of containers containing only plasma is prepared for purposes of comparison. A third container is prepared containing 1 mL of patient plasma with unknown concentration of TSI. To each sample is added 475 µL of reconstituted fibrinogen solution and 50 µL reconstituted thrombin. The clotting time is then measured. Steps a to f may be used as a research tool to evaluate activity of TSI's. However, as more is known about the effect on QTT of various concentrations of a particular TSI, the running of a standard to obtain the curve may be unnecessary. In such instances, the QTT alone without the comparison testing will be sufficient to allow practitioners to evaluate concentration of TSI in the blood.

As an alternative, the kit may contain only fibrinogen and thrombin, whilst one or more stock solutions containing appropriate concentrations of TSI in plasma is maintained for use in the test. (It would also be possible to have one stock concentration at highest level to be tested, which would be diluted to provide lower concentrations for use to provide the appropriate curve.) The extent to which stock solutions are used or multiple vials of TSI containing differing amounts of TSI are provided will depend on the number of tests done in any particular health care center and the quality of staff available to provide testing services. All of the components, plasma, thrombin, and fibrinogen, should be used fresh or be frozen to avoid loss of potency. All of the agents used, including plasma with TSI, normal plasma, thrombin, and fibrinogen may be provided as lyophilized materials in vials for reconstitution. Once reconstituted, the active components are easily inactivated.

Among the uses for which the invention is suitable include quantitative clinical monitoring of patients anticoagulated with the thrombin-specific agents and laboratory research in animal models of thrombosis.

What is claimed:

1. A method of measuring quantitative thrombin time comprising the steps of:

(1) preparing a composition comprising plasma in buffer to obtain a concentration of about 1:10 plasma to buffer;

(2) preparing a fibrinogen mixture comprising fibrinogen concentration of about 0.1 to 18 µM fibrinogen in buffer;

(3) preparing a composition containing a concentration of about 2.5 to 20 U/mL alpha-thrombin in buffer;

(4) preparing a mixture comprising equal amounts of the compositions obtained in steps (1) and (2);

(5) placing in an assay well an aliquot of the mixture prepared in step (4) and an aliquot of the mixture prepared in step (3); and (6) determining the amount of time required for clot formation.

2. The method of claim 1 wherein the mixture prepared in step (2) is at a concentration of 9 to 18 µM fibrinogen in buffer.

3. The method of claim 1 wherein, in step (5), the ratio of amount of reactants is 2 parts of the mixture obtained in step (4) to 1 part of the mixture obtained in step (3).

4. A kit comprising:

1. at least one vial of lyophilized fibrinogen, 2. at least one vial containing thrombin, and 3. instructions for evaluating quantitative thrombin time (QTT) according to the method of claim 1.

5. The kit of claim 4 further comprising at least one vial of plasma.

6. The kit of claim 4 further comprising at least one vial of a thrombin-specific inhibitor.